United States Patent [19]

DiSalvo et al.

[11] 4,379,094
[45] Apr. 5, 1983

[54] FERROSILOXANE THERMAL STABILIZERS FOR DIORGANOPOLYSILOXANES

[75] Inventors: Gail D. DiSalvo, Greenwich; James D. Reedy, New Fairfield, both of Conn.

[73] Assignee: Union Carbide Corporation, Danbury, Conn.

[21] Appl. No.: 335,613

[22] Filed: Dec. 30, 1981

[51] Int. Cl.$^3$ .......................... C07F 15/02; C07F 7/08
[52] U.S. Cl. .................................. 260/439 R; 556/401
[58] Field of Search ..................... 556/401; 260/439 R

[56] References Cited

U.S. PATENT DOCUMENTS

| | | |
|---|---|---|
| 2,389,802 | 11/1945 | McGregor et al. ................. 556/401 |
| 2,445,567 | 7/1948 | Elliott ............................... 260/448.2 |
| 3,002,927 | 10/1961 | Awe ................................. 556/401 X |
| 3,002,989 | 10/1961 | Awe et al. ........................... 556/401 |
| 3,267,031 | 8/1966 | Buehler ........................... 556/401 X |
| 3,352,781 | 11/1967 | Buehler ............................... 252/37.2 |
| 3,865,784 | 2/1975 | Neale et al. ..................... 556/401 X |
| 3,884,950 | 5/1975 | Koda ................................... 556/401 |
| 4,070,343 | 1/1978 | Kishimoto et al. ............. 556/401 X |
| 4,264,459 | 4/1981 | Hafner et al. ................... 556/401 X |

*Primary Examiner*—Paul F. Shaver
*Attorney, Agent, or Firm*—Paul W. Leuzzi, II

[57] ABSTRACT

Ferrosiloxane compounds prepared by reacting iron carboxylates and N,N-disubstituted silylamines are useful as thermal stabilizers for diorganopolysiloxanes. The thermally stable diorganopolysiloxanes find utility as heat transfer fluids, high temperature lubricants, hydraulic fluids and electric insulating fluids, to name but a few.

7 Claims, No Drawings

FERROSILOXANE THERMAL STABILIZERS FOR DIORGANOPOLYSILOXANES

BACKGROUND OF THE INVENTION

This invention generally relates to novel ferrosiloxanes compounds and their use as heat stabilizers for diorganopolysiloxanes. More particularily, the invention relates to those ferrosiloxane compounds made from iron carboxylates and N,N-disubstituted silylamine.

It is well recognized in the art that diorganopolysiloxanes are susceptible to breakdown through dipolymerization and oxidation upon exposure to temperatures in excess of 300° C. for prolonged periods of time. This dipolymerization and oxidation ultimately results in a gelling of the diorganopolysiloxane. Various methods of stabilization have been proposed in the prior art to solve this problem. In most instances, soluble or partially soluble forms of transition metal compounds have been directly added to the siloxane polymer to be stabilized without further treatment of the resulting mixture as seen, for example, by the proposed use of carboxylate salts of iron, cobalt, nickel and copper as antioxidants in U.S. Pat. No. 2,445,567. The use of other types of antioxidants has also been proposed, e.g., ferrocenyl-substituted siloxanes, as seen in Chemical Abstracts, 72, page 32,635 P (1970) and U.S. Pat. No. 3,679,660, and iron oxide as proposed by U.S. Pat. No. 3,352,781. Recently, U.S. Pat. No. 3,002,927 has taught the use of iron salts of carboxylic acid along with mechanical aeration at greatly elevated temperatures of the siloxane mixture prior to use. The most recent method to overcome this problem is found in U.S. Pat. No. 3,865,784 which proposes that a mixture of a diorganopolysiloxane compound and an iron carbonyl compound, heated to at least 120° C. in the presence of oxygen, produces a stabilized iron-containing diorganopolysiloxane.

Recent art relying upon non-ferrous materials include U.S. Pat. No. 3,884,950 which proposes the use of a cerium salt of an organic carboxylic acid soluble in aromatic hydrocarbons. Finally, Japanese KoKai No. 79/32,563 proposes the use of the reaction product of siloxanes with cerium carboxylates to improve the heat stability of the siloxanes.

The increasing importance of thermally stable diorganosiloxanes warrants a continuing search for novel stabilizer that are at once commercially feasible and yet effective in their applicability to the task at hand. Other objects and advantages of this invention will become readily apparent from the detailed description and appended claims.

SUMMARY OF THE INVENTION

The present invention provides novel ferrosiloxane compounds and their use as heat stabilizers for diorganopolysiloxanes. The novel ferrosiloxane compounds of the present invention can be prepared by reacting iron carboxylates with N,N-disubstituted silylamine to form compounds of the formula:

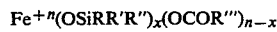

wherein n is the oxidation state and has a value of 2 or 3; x has a value of 1 to 3 inclusive; R, R', R" and R'" are individually an alkyl, alkaryl, alkenyl, alkynyl, aryl, cycloalkyl, heteroatom substituted alkyl, cycloalkyl or aryl group having from 1 to 25 carbon atoms; R' could also be hydrogen or a silyl group and wherein R" could also be a siloxy or substituted siloxy group.

DETAILED DESCRIPTION OF THE INVENTION

In accordance with the present invention there is provided novel ferrosiloxane compounds useful as thermal stabilizers for diorganopolysiloxanes. The ferrosiloxane compounds are prepared by mixing the iron carboxylate with a N,N-disubstituted silylamine at room temperature or above. The reaction mixture does not have to be processed further, it can be employed as is. This mixture has a viscosity and solubility such that it has good compatibility with the diorgano-polysiloxanes. Such a combination of easy preparation and compatibility in the diorganopolysiloxanes is difficult to achieve with any of the stabilizers previously known in the art.

Suitable iron carboxylates for the preparation of the ferroxilosane include; but are not limited to, ferrous carboxylates such as diacetate, dilaurate, dioctoate, neodecanoate and the like or ferric carboxylates such as triacetate, trilaurate, trioctoate and the like. It is preferred that the iron carboxylate contains at least five carbon atoms.

Suitable N,N-substituted silylamines for the preparation of the ferrosiloxane include, but are not limited to, $Me_xSi(NMe_2)_{4-x}$, $Me_2NSiMe_2(OSiMe_2)_aNMe_2$, $HSi(NMe_2)_3$, $Me_3Si(OSiMe_2)_a[OSi(NMe_2)Me]_bOSiMe_3$, N,N-dimethylaminotrimethylsilane, N,N-dimethylamino tricyclohexylsilane, N,N-ethylhexylaminotripropylsilane, N,N-dioctylaminotrioctylsilane and N,N-dibutylaminotrioctadicylsilane. It is preferred that the silylamine be a dimethylamino containing silane or a siloxane.

In carrying out the reaction between the silylamine and the iron carboxylate, it is recommended that the reaction temperature be kept below the point where significant formation of Si—O—Si or Fe—O—Fe bonds occur, generally this is about 100° C. The product should not be heated above 100° C. until it is diluted to its appropriate use level. It is also recommended that any substituted or unsaturated reactants are chosen so as not to be deleterious in their interaction to the Si—N bond of the silylamine or the Si—O—Fe bond of the final product. Such reactants to be avoided include those containing hydroxyl groups, silanols and those contaminated with water.

The novel ferrosiloxane prepared is of the general formula:

wherein R,R'R",R'", n and x are as previously defined. It is preferred that R,R',R" and R'" contain no more than twenty-five carbon atoms and more preferably no more than twelve. It is also preferred that the R, R', R" or R'" groups are individually unsubstituted alkyl groups.

The stabilized iron-containing diorganopolysiloxane products of this invention have a wide range of utility in the field of high temperature service that is well known in the art. For instance, they can be used as heat transfer fluids such as, radiator fluids, quenching baths for metal parts, etc.; high temperature greases and lubricants such as, in the manufacture of synthetic fibers, etc.; hydraulic fluids such as, the coupler fluid for an automotive fan clutch, etc.; electrical insulating fluids, and the like.

Whereas the exact scope of the instant invention is set forth in the appended claims, the following specific examples illustrate certain aspects of the present invention and, more particularly, point out methods of evaluating the same. However, the examples are set forth for illustration only and are not to be construed as limitations on the present invention except as set forth in the appended claims. All parts, percentages and proportions are by weight unless otherwise specified.

EXAMPLE 1

To 12.7 parts (0.024 mole) of ferric octoate (10.5% Fe) is added 8 cc (0.05 mole) of N,N-dimethylaminotrimethylsilane in 5 ml portions. The temperature of the reaction mixture is allowed to rise from 26° to 42° C. during the addition. The solution is stirred at room temperature for 3 to 4 hours. The reaction solution is characterized by ir spectroscopy: intense bands at 850 $cm^{-1}$ and 900 $cm^{-1}$ were characteristic of a trimethylsiloxy group attached to a metal atom. Elemental analysis found: Fe, 6.89, Si, 8.00. Theoretical values, based on added ingredients: Fe, 6.05, Si, 10.07. The low silicon value may be due to the analytical technique or to the loss of volatile silylamine.

The reaction mixture, a reddish brown homogenous liquid, is not further purified. By-product amide and unreacted starting materials are not removed. The mixture is used as a stabilizer for silicone oils by adding the stabilizer to the oil in the amount required to achieve 200–300 ppm of iron content. Comparisons with iron (III) octoate, used commercially, and with the iron stabilizer of U.S. Pat. No. 3,865,784, a stabilizer made from iron pentacarbonyl, Fe(CO)$_5$ and silicone oil at elevated temperature are shown in Tables I and II. At 325° C. (Table I), the stabilizer made from the iron carbonyl compound (7265/500) is as good or slightly better than the stabilizer of the instant invention, however, the preparation of the stabilizer from iron carbonyl involves the use of a very toxic material and some difficulties have been found in making the stabilizer reproducibly. The stabilizer of our invention is easily and reproducibly made from materials of low toxicity and in contrast to U.S. Pat. No. 3,865,784 can be prepared as a concentrate and added to silicone fluids with no additional processing.

As shown in Table I, the stabilizer of our invention is much more effective than is ferric octoate, the commercial material, for stabilization of the low viscosity dimethylsilicone oil exposed to 325° C. temperature. At 325° C., the data have a wide range; this is true for both of the experimental stabilizers—7265 and our invention.

At 317° C. (Table II), the superiority of our novel stabilizer over iron octoate is apparent. The iron carbonyl-prepared stabilizer is also very good. Without a stabilizer, the dimethylsilicone oil (100 cstk) is deteriorated within 24 hours. The phenylmethylsilicone oil, which is widely used for high temperature applications, is also less stable at 317° C. than is the dimethylsilicone oil stabilized with our novel stabilizer.

An advantage of our invention is that it provides a stabilized diorganopolysiloxane which is more heat resistant than phenylmethylsilicone oil. A stabilized dimethylsilicone oil would be considerably less expensive than phenylmethylsilicone oil.

TABLE I

Thermal Stability of Silicone Oils - Stabilized and Unstabilized

| Oil[1] | Stabilizer (ppm Fe)[3] | Time to Gel (at 325° C.)[2] (hours) |
|---|---|---|
| A 50 centistoke | none | <3 |
| A 50 centistoke | 200[1] | 72 |
| A 100 centistoke | none | <3 |
| A 100 centistoke | 200[1] | 72, 192, 288 |
| A 100 centistoke | 200 (Ferric Octoate) | <24 |
| A 350 centistoke | none | <3 |
| A 350 centistoke | 200[1] | 72 |
| A 1000 centistoke | none | <3 |
| A 1000 centistoke | 200[1] | 72 |
| B | none | 72 |
| C 500 centistoke | 350 | 168 |

[1]Stabilizer of Example 1 used in amount to achieve 200 ppm of iron content in 50 grams of oil.
[2]Heated in a 100 ml open beaker in a muffle furnace.
[3]Iron contents of samples were determined by atomic absorption.
Oil A - Dimethylsilicone oil
Oil B - Phenylmethylsilicone oil
Oil C - Iron-carbonyl stabilized dimethylsilicone oil

TABLE II

Thermal Stability of Silicone Oils

| Oil[1] | Stabilizer (ppm Fe)[3] | Time to Gel (at 317° C.)[4] (hours)[5] |
|---|---|---|
| A | none | <24, <24 |
| C | 350[3] | 161, 173 |
| A | 300[1] | <164, <264 |
| A | 470[1] | 161, 173, 212, 284 |
| A | 750[2] | 115 |
| B | none | 92, 92, 115, 137 |

[1]Stabilizer of Example 1 in 50 grams of oil.
[2]Ferric octoate in 50 grams of oil.
[3]Iron contents determined by atomic absorption.
[4]Heated in open beaker in muffle furnace.
[5]Values represent separate experiments.
Oil A - Dimethylsilicone oil, 100 centistokes
Oil B - Phenylmethylsilicone oil
Oil C - Iron-carbonyl stabilized dimethylsilicone oil, 500 centistokes

We claim:

1. A ferrosiloxane compound of the formula:

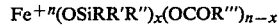

$$Fe^{+n}(OSiRR'R'')_x(OCOR''')_{n-x}$$

wherein n has a value of 2 or 3; x has a value of 1 to 3 inclusive; R, R', R" and R''' are individually are alkyl, alkaryl, alkenyl, alkynyl, aryl, cycloalkyl, heteroatom substituted alkyl, cycloalkyl or aryl group having from 1 to 25 carbon atoms; R' could also be hydrogen or a siloxy group and wherein R" could also be a siloxy or substituted siloxy group.

2. The compound of claim 1 wherein R, R' and R" are siloxy groups.

3. The compound of claim 1 wherein R''' has at least five carbon atoms.

4. A process for stabilizing diorganopolysiloxanes from heat by adding an effective amount of a ferrosiloxane compound of the formula:

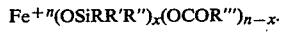

$$Fe^{+n}(OSiRR'R'')_x(OCOR''')_{n-x}.$$

5. The process of claim 4 wherein the diorganopolysiloxane being stabilized is a trimethylsiloxy-end blocked dimethylsiloxane.

6. A process for stabilizing diorganopolysiloxane from heat which comprises adding an effective amount of an iron carboxylate and an effective amount of a N,N-disubstituted silylamine.

7. The process of claim 6 wherein the diorganopolysiloxane being stabilized is a trimethylsiloxy-end blocked dimethylsiloxane.

* * * * *